United States Patent
Poole et al.

(10) Patent No.: US 6,497,051 B1
(45) Date of Patent: Dec. 24, 2002

(54) DIGITAL MEASURING DEVICE

(76) Inventors: Wayne F. Poole, 6820 Hwy. 70 South, Apt. 410, Nashville, TN (US) 37221; Michael G. Sills, 9898 E. Alabama Pl., Building 8, Apt. 301, Denver, CO (US) 80231

( * ) Notice: Subject to any disclaimer, the term of this patent is extended or adjusted under 35 U.S.C. 154(b) by 0 days.

(21) Appl. No.: 09/290,849

(22) Filed: Apr. 13, 1999

Related U.S. Application Data

(60) Provisional application No. 60/082,239, filed on Apr. 16, 1998.

(51) Int. Cl.$^7$ .................................................. B43L 9/02
(52) U.S. Cl. ...................... 33/784; 33/558.01; 33/27.02
(58) Field of Search ..................... 33/784, 26, 27.02, 33/558.01, 1 C, 1 G, 1 AA, 1 CC, 773

(56) References Cited

U.S. PATENT DOCUMENTS

| | | | |
|---|---|---|---|
| 2,557,428 A | | 6/1951 | Grostic |
| 3,113,381 A | | 12/1963 | Khol |
| 3,354,551 A | * | 11/1967 | Overby .................. 33/558.01 |
| 3,816,928 A | * | 6/1974 | Fessenden .................. 33/1 C |
| 4,270,273 A | | 6/1981 | Berger |
| 4,388,759 A | | 6/1983 | Orejola |
| 4,468,860 A | * | 9/1984 | Rodengen .................. 33/1 PT |
| 4,612,656 A | | 9/1986 | Suzuki et al. |
| 4,839,833 A | | 6/1989 | Parhiskari |
| 4,845,646 A | * | 7/1989 | Marquis et al. .............. 364/560 |
| 4,915,112 A | | 4/1990 | Singer |
| 4,941,267 A | | 7/1990 | Miller, Jr. |
| 5,022,162 A | * | 6/1991 | Luikko .................. 33/784 |
| 5,154,003 A | * | 10/1992 | Moore .................. 33/558.01 |
| 5,253,431 A | * | 10/1993 | Smith .................. 33/810 |
| 5,327,907 A | | 7/1994 | Fischer |
| 5,337,488 A | * | 8/1994 | Lemelson .................. 33/784 |
| 5,430,954 A | * | 7/1995 | Best et al. .................. 33/784 |
| 5,560,119 A | * | 10/1996 | LeBreton .................. 33/773 |
| 5,875,561 A | * | 3/1999 | Chen et al. .................. 33/784 |

OTHER PUBLICATIONS

Precision Technology Devices, Inc. Brochure, *AccuTracker*, Aug. 11, 1996.

\* cited by examiner

*Primary Examiner*—Diego Gutierrez
*Assistant Examiner*—Lydia M. DeJesús
(74) *Attorney, Agent, or Firm*—Pearne & Gordon LLP

(57) ABSTRACT

A measurement device having a pair of legs. Each leg has a measurement point and a fulcrum end, the fulcrum ends providing a pivot point for the legs so that the measurement points arcuately move apart from one another. The measurement device has a transducer assembly connected to at least one of the legs which measures leg displacement and generates a distance signal. The measurement device has a programmable processing unit adapted to process the distance signal and display a distance measurement on an electronic display.

20 Claims, 2 Drawing Sheets

DIGITAL MEASURING DEVICE

This application claims the benefit of U.S. Provisional Application No. 60/082,239, filed Apr. 16, 1998.

BACKGROUND OF THE INVENTION

The present invention relates to measurement devices. More specifically, the present invention relates to a hand held measuring instrument, such as a compass, used to measure scaled or unscaled distances on a surface.

A wide variety of measurement device are known in the art. Examples of simple measurement devices include rulers and tape measures. More complex devices include rulers with sliding or rotating position indicators. Also known are compasses and calipers having mechanical or electronic displays. Examples of a variety of measurement devices are described in U.S. Pat. Nos. 2,557,428, 3,113,381, 4,270,273, 4,388,759, 4,612,656, 4,839,833, 4,915,112, 4,941,267, and 5,327,907, each of which are wholly incorporated herein by reference. Other devices include rolling measurement devices used to trace an arc or a convoluted boundary.

However, these measurement devices fail to provide a simple, yet highly accurate measurement device for use in applications where measurements are based on a printed scale and where a high degree of precision is required. These applications include taking measurements on a variety of medical scans, such as X-ray films, radiographs, computed tomography (CT), magnetic resonance (MR), ultrasound nuclear medicine and the like. Similar measurement devices are required in other medical applications, such as medical physics and cardiology where the measurement of heart rates and timing of events in the cardiac cycle are necessary. Non-medical applications often require accurate measurements on scaled medium. These include, for example, architectural or engineering drawings, aeronautical and nautical navigation charts, and clothing pattern designs.

More specifically, the prior art measurement devices suffer from one or more of the following disadvantages. Most of the prior art devices have a design that is unfamiliar to the average user and, therefore, require a learning process to be used properly. Many require two hands to use. Most only work well when placed on a planar surface, rather than in situations where a linear measurement in three dimensional space is needed. Other designs, such as rolling measurement devices, do not trace straight lines well and can only approximate linear distances. Other designs have structural features that block the user's view of the item measured, the boundary of the item or the area surrounding the measured item.

SUMMARY OF THE INVENTION

The present invention overcomes these disadvantages by providing a measurement device having a pair of legs. Each leg has a measurement point and a fulcrum end, the fulcrum ends providing a pivot point for the legs so that the measurement points arcuately move apart from one another. The measurement device has a transducer assembly connected to at least one of the legs which measures leg displacement and generates a distance signal. The measurement device has a programmable processing unit adapted to process the distance signal and display a distance measurement on an electronic display.

BRIEF DESCRIPTION OF THE DRAWING

These and further features of the present invention will be apparent with reference to the following description and drawings, wherein.

DETAILED DESCRIPTION OF THE INVENTION

Figure 1:
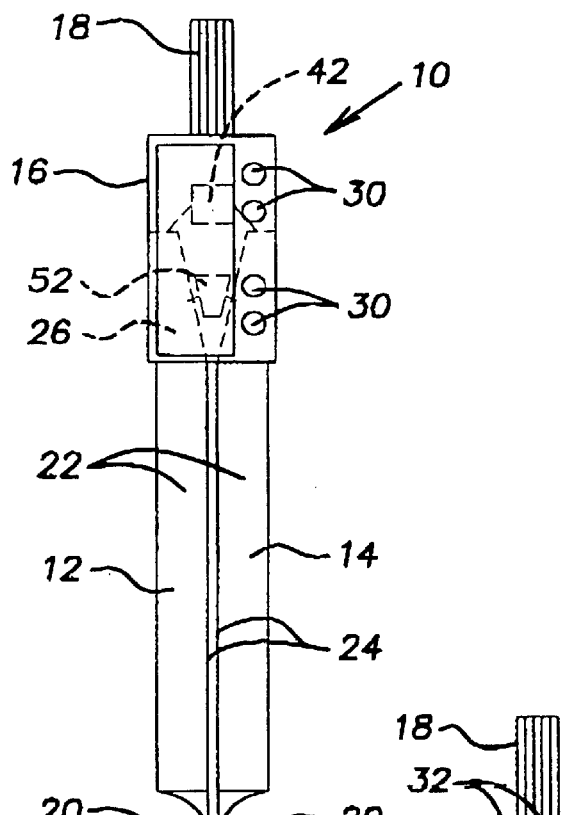
FIG. 1 is a front elevational view of a measurement device according to the present invention showing some features in phantom.

In the detailed description which follows, identical components have been given the same reference numerals, and, in order to clearly and concisely illustrate the present invention, certain features may be shown in somewhat schematic form.

With reference to all of the figures, the present invention provides an electronic measurement device for measuring distances. The measurement device provides a pair of legs which move in a known or a fixed relationship to each other, such as the legs of a compass or caliper. Compasses and calipers are generally understood to be measurement devices where the legs arcuately move apart from one another at one end, while being pivotally fixed together at a second end. The illustrated, and preferred, example of the measurement device is such a compass and will be referred to herein as a digital measurement device, or compass 10. One skilled in the art will appreciate that the present invention can be adapted for use in a slide caliper design. A slide caliper is generally known to be a measurement device where the legs move apart from one another, but stay in a parallel relationship.

The compass 10 provides a first leg 12 and a second leg 14. The compass 10 also provides a housing 16 and, optionally, a handle 18. The legs 12, 14 each have a first or measurement end 20, a longitudinal body 22 having an inside edge 24 and a second or fulcrum end 26. The fulcrum ends 26 are disposed in and retained by the housing 16. The fulcrum ends 26 provide a pivot point for the legs 12, 14. Mounted on the housing 16 are an electronic display 28 such as an LCD, user switches or buttons 30, and input/output (I/O) ports 32. The user buttons 30 control compass 10 functions, including for example, an on/off button 34, a mode button 36, a calibrate button 38 and a scale button 40. The buttons 30 are preferably touch or pressure sensitive temporary switches, but can alternatively be toggle switches, keys, or other input or signaling devices. The housing 16 contains additional components including a transducer assembly 42, a power source 44, and analog to digital converter 46 and a programmable processing unit or CPU 48. The handle 18 serves as a convenient place for the user to grasp the compass 10 and can optionally serve as a position locking mechanism for the legs 12, 14. If used as a lock, the handle 18 is turned to actuate a lock device, such as a cog or gear, used to keep the legs 12, 14 from moving.

Figure 2:
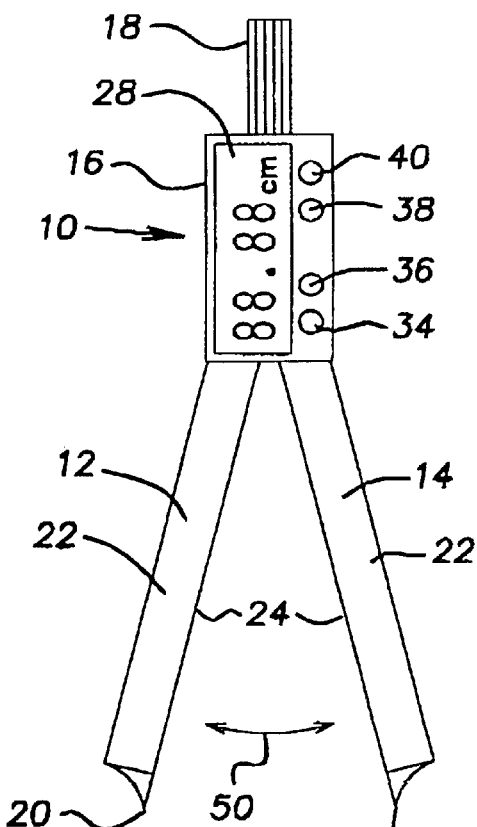
FIG. 2 is another front elevational view of the measurement device.
Figure 3:
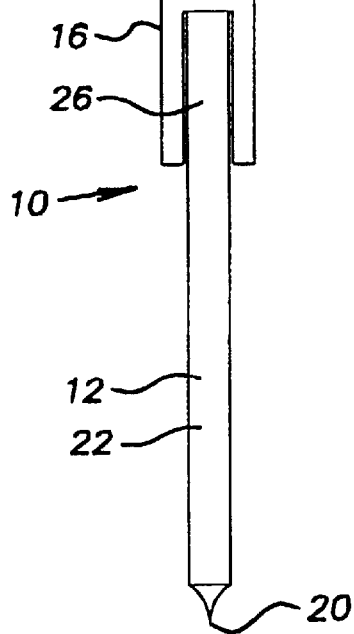
FIG. 3 is a side elevational view of the measurement device.
Figure 4:
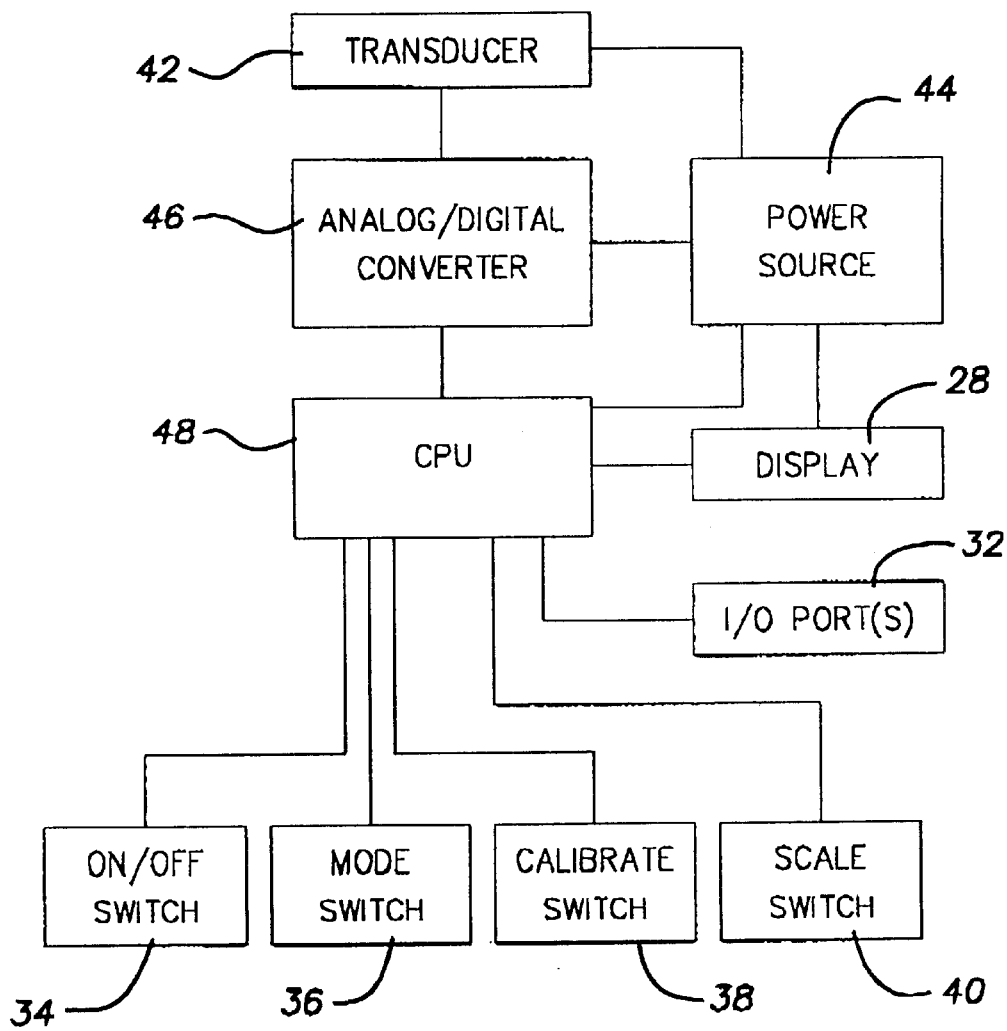
FIG. 4 is an electrical block diagram of the measurement device.

The legs 12, 14 are adapted to pivot at the fulcrum ends 26 in opposite directions as indicated in FIG. 2 by arrow 50. In a closed position, the inside edges 24 of the legs 12, 14 may be slightly spaced apart as illustrated in FIG. 1, lie flat against each other, or make a point contact with each other. The legs 12, 14 can move independent of one another where each leg 12, 14 has the ability to move a different arcuate amount than the other. More preferably, the angular movement of the legs 12, 14 are dependent to each other. As will be more fully discussed herein, the legs 12, 14 are spread apart and used to take measurements. In other words, the distance between specific points on the legs 12, 14 is the distance to be measured. Preferably, the specific measurement point is the measurement end 20. Preferably, the measurement end 20 is tapered to a sharp point for accurate placement and to avoid blocking the user's view. One skilled in the art will appreciate that measurements can be taken based on any preselected point on the legs 12, 14, and the selected point will herein be referred to as a measurement point. The movement of the legs 12, 14 must be precise and accurate. Precise and accurate movement can be accomplished through the use of a gear type mechanism, or gearing assembly 52, connected to each of the fulcrum ends 26. To achieve dependent angular movement of the legs 12, 14, the gearing assembly 52 preferably is arranged to result in a direct one to one (1:1) motion between the two legs 12, 14.

Figure 5:
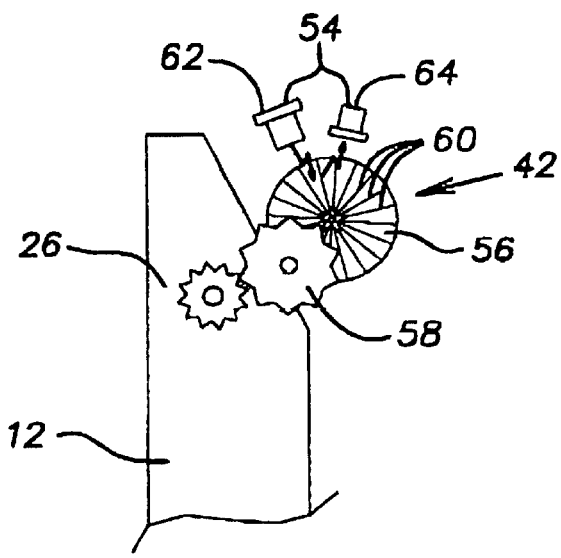
FIG. 5 is a schematic diagram of a preferred embodiment of a transducer for use with the measurement device.

The mechanical movement of the legs 12, 14 is preferably converted into an electrical signal indicative of the distance between the measurement ends 20, or distance signal. Converting the mechanical movement of the legs 12, 14 into a distance signal can be accomplished using a variety of transducer assemblies 42. The preferred embodiment of a transducer assembly 42 is schematically illustrated in FIG. 5 and is an optical sensor 54 adapted to sense motion of a wheel 56. The wheel 56 is actuated by at least one of the legs. Preferably, the wheel 56 is circular, annular or semicircular and has a rotational motion about an axis. One skilled in the art will appreciate that the wheel 56 may have other forms such as a sliding bar or pendulum type device. In the illustrated embodiment, the wheel 56 is a circular disk and the leg 12 drives a gear 58 which drives the wheel 56. An example driving mechanism for the gear 58 and wheel 56 are pinions respectively located on the leg 12 and the wheel 56. The wheel 56 is preferably etched with a laser to provide the wheel 56 with a series of scores 60. As the wheel 56 rotates, the scores 60 are counted by the optical sensor 54 as the wheel 56 rotates. The optical sensor 54 preferably provides a small LED 62 that transmits light onto the wheel 56 and an optical pick-up 64 compatible with the wavelength of light transmitted by the LED 62. The optical pick-up 64 senses light reflected by the wheel 56. The scores 60 act to disrupt or polarize the reflected light. The scores 60 are preferably very thin and arranged on the wheel 56 in a high density pattern to achieve a high degree of accuracy and very high definition or resolution, preferably being proportional to leg movement in the tenths or hundredths of millimeters.

Other types of transducer assemblies 42 can be used to produce the distance signal. Examples of such transducer assemblies 42 include gearing adapted to turn a small variable resistor, capacitor, or inductor, thereby creating a measurable difference in voltage, current, power, frequency or any other electrical signal. Another possibility includes a strain-gauge transducer.

In any of the foregoing transducer assembly 42 embodiments, proper gearing or leverage will result in a large transducer movement for a small movement of the legs 12, 14. Pulleys or ratio arms may also be used with the gears to obtain the desired leverage at the transducer, or may replace the gears.

A transducer assembly 42 connected directly to the legs 12, 14 of the device is also contemplated. This would eliminate the need for gears to drive the transducer assembly 42. One approach involves the use of a potentiometer, having a sliding wiper, mounted at the intersection of the caliper's legs 12, 14.

In most cases, the output from the transducer assembly 42 is an analog distance signal. The analog to digital converter 46 converts the analog distance signal to a digital distance signal which is processed by the CPU 48. Preferably the analog to digital converter 46 has a fine resolution, or high accuracy. Generally, suitable resolution is achieved by using an analog to digital converter 46 with an output having a large number of bits. As will be more fully discussed below, the CPU 48 is preferably programmed to process the digital distance signal and display a distance result on the display 28. Most of the contemplated transducer assemblies measure angular motion or correspond to angular motion of the legs 12, 14. Accordingly, part of the CPU's 48 processing preferably includes compensating for the circular path of the measurement ends 20 as measured by the specific transducer assembly 42 used. Since the legs 12, 14 move in an angular motion, the absolute linear distant the measurement ends 20 of the legs 12, 14 travel apart from one another must be derived from the angular relationship of the legs 12, 14. The displacement of each measurement end 20 from a starting point is computed by using known trigonometric principles, such as solving the equation: displacement=(leg length)×sin (angle of displacement). The leg length is measured from the fulcrum end 26 to the measurement end 20. In the illustrated embodiment, the distance is preferably measured along the inside edge 24 since the measurement end 20 is disposed in a linear relationship with the inside edge 24.

The transducer assembly 42, analog to digital converter 46, CPU 48 and display 28 are powered by the power source 44. The power source 44 is preferably a self contained power source requiring no connection outside the compass 10, such as a replaceable battery retained by the housing 16. Alternatively, the compass 10 can be provided with electrical power from an external power source 44. In that case, the compass 10 is provided with a connector to receive a power cable.

The compass 10 is optionally interfaced to peripheral devices to directly input distance measurements into the peripheral device. For this purpose, the measurement device is preferably provided with the input/output port(s) 32. The input/output port(s) 32 transmit a distance measurement signal to the peripheral device. The input/output port(s) 32 can include one or more type of interfaces to communicate with a variety of commercially available products. Possible interfaces include an infrared communication port, a uni-directional or bi-directional serial interface, or a PACS interface to display measurement information on a video monitor or integrate measurement information with other image data for display and storage with the image. Potential peripheral devices include a printer for documentation of measurements and a computer for storage of acquired measurement data or manipulation of the data. Using a bi-directional interface, the compass 10 can be programmed with additional features.

Operation of the compass 10 will now be discussed. To conserve power, the compass 10 is normally turned off. To take a measurement, the user first turns the compass 10 on by pushing the on/off button 34. The compass 10 can be programmed to turn itself off after a predetermined period of time has elapsed during which the compass 10 has not been used. Next, a measurement output mode of the caliper is set by the user by pressing the mode button 36. The selectable modes preferably include taking English measurements (e.g., inches or fractional inches) and taking metric measurements (e.g., centimeters). Other modes can include comparative measurements where the compass 10 is programmed to display whether a first measurement is the same, smaller than or larger than a second measurement. The compass 10 can also be programmed to display the difference between the first measurement and the second measurement in English or metric units. This type of measurement is particularly useful in tracking the growth of an object over time. For instance, the size of an tumor shown on a radiological film can be easily compared to an earlier film. Another selectable mode preferably includes selection of how many decimal places the user wishes to be displayed. The compass 10 can be preprogrammed to select a default mode which is most used by the user.

The user is able to select a scale by depressing the scale button 40. This feature is useful when the measurement to be taken is printed on a sheet drawn in a particular scale. In that case, the user uses the scale button 40 to select the same scale used by the printout. When the measurement ends 20 are placed on the printout to measure a distance, the CPU 48 will automatically compensate for the scale and display an unscaled measurement. For example, if a MRI image of a person is printed in centimeters and uses a scale of one to four, the compass 10 can be set for taking measurements in centimeters and a scale of one to four. If a measurement of the size of an organ is taken where the measurement ends 20 are spaced two centimeters apart on the MRI image, the CPU 48 will automatically calculate the actual distance and display a measurement of eight centimeters on the display 28.

The user is also able to calibrate the compass 10 to a known distance. The known distance need not have a scale that is one to one. When calibrated, any subsequent measurements would be based on the initial calibration. To calibrate the compass 10, the legs 12, 14 are separated a known distance and the known distance is entered into the CPU 48 by sending a calibration signal to the CPU 48. This is preferably accomplished by placing the measurement ends 20 against a legend and pressing the calibration button 38. The CPU 48 then automatically computes and displays subsequent measured distances, as a function of leg movement, based on the initial calibration. The measurement display may either be updated continuously as the legs 12, 14 move, or only when another button is pressed or the calibration button 38 is pressed again. The measurement of a brain tumor on an MRI image will serve as an example of the compass 10 using the calibration technique. The user first places the legs 12, 14 of the compass 10 over a printed image legend and separates the legs 12, 14 so that the measurement ends 20 are spread on marks on the legend corresponding to a reference distance referred to as Xref. The calibrate button 38 is then pressed to calibrate the measurement device to the Xref distance. This will calibrate the measurement device to read precisely a calibrated distance, or Xcal. It is understood that Xcal can be set and reset to any distance on the printed image scale (e.g., 1 cm, 3 cm, 5 cm, or the like). For an MRI image, 3 cm is a logical choice since 3 cm lies near the midrange of distances measured on a typical radiology exam. The measurement device is then used to measure the lesion in question by moving and positioning the legs 12, 14 of the measurement device. As the legs 12, 14 move, the digital display 28 will increase or decrease correspondingly in a programmed fashion to display 28 the exact size of the lesion relative to Xcal. To measure an object on a different calibration distance, Xref, the measurement device is recalibrated.

The present invention has intrinsic advantages over prior art measurement devices. Linear measurements with a digital compass 10 is a rapid, one-hand task. The hand-held compass 10 design is familiar to almost everyone, and requires no or little learning to be utilize properly. This is especially true in fields such as radiology or drafting, where non-digital compasses are an everyday implement.

The compass 10 measures the straight-line distance between its two subtended legs 12, 14. This is ideal where measurements are required in orthogonal coordinates or as a function of height, width, and length. In comparison, a roller-ball mechanism is used to mainly to trace an arc or convoluted boundary and may lead to erroneous linear distance measurements when attempting to make direct point to point measurements since linear measurements are only as accurate as one can trace a straight line free-hand. One could use a straight edge to obtain linear measurements with a roller-ball device, but this necessitates the use a second implement to obtain the desired measurement and detracts from the device's ease of use.

Furthermore, positioning of the compass 10 merely requires placing one measurement end 20 on a first point, or point A, and spreading the legs 12, 14 so that the other measurement end 20 is placed on a second point, or point B. When the legs 12, 14 are spread, the desired distance is read off the digital display 28. A roller-ball device would similarly be placed at point A and then rolled toward point B until the desired distance has been transversed and then the measurement is obtained. Assuming the distance between points A and B has been transversed in a perfectly linear fashion, there is still the possibility of over or undershooting point B during the roll between points A and B. This would require repeating the operation until the user is satisfied with the trace, and would incorporate another possible measurement error. Even if the measuring device is intrinsically accurate, the overall reliability of the device will hinge on the ability to obtain a reproducible measurement result. It is much easier to obtain reproducible measurements from a compass design than from a track-ball. This affords greater precision to the digital compass design of the present invention.

The compass 10 can be used as a reference by opening the legs 12, 14 to a known distance and using the compass 10 to determine whether items are smaller or larger than the preset distance. This function can not be performed using a rolling ball device.

Although particular embodiments of the invention have been described in detail, it is understood that the invention is not limited correspondingly in scope, but includes all changes and modifications coming within the spirit and terms of the claims appended hereto.

What is claimed is:

1. A measurement device comprising,
   a pair of legs, each leg having a measurement point and a fulcrum end, the fulcrum ends each providing a pivot point for a respective one of said legs so that the measurement points are adapted to arcuately move apart from one another;
   a transducer assembly connected to at least one of the legs and adapted to measure leg displacement and generate a distance signal;
   a programmable processing unit adapted to process the distance signal and display a distance measurement on an electronic display; and
   a control for selecting a scale value so that the programmable processing unit compensates for a scale associated with a measurement taken between the measurement points and displays an unscaled measurement on the display, wherein the scale lacks predetermined scale values, such that the scale value is set, based on said measurement, to any value within a given range.

2. The measurement device according to claim 1, wherein the transducer assembly is an optical sensor adapted to sense motion of a wheel, the wheel being actuated by at least one of the legs.

3. The measurement device according to claim 2, wherein the wheel has a series of scores, the scores being counted by the optical sensor as the wheel is actuated.

4. The measurement device according to claim 1, wherein the programmable processing unit is programmed to compensate for an arcuate path of the measurement points.

5. The measurement device according to claim 1, wherein the legs move independently of each other.

6. The measurement device according to claim 1, further comprising a gearing assembly connected to each of the legs so that movement of the legs depend on each other.

7. The measurement device according to claim 1, wherein the distance signal generated by the transducer is an analog distance signal and an analog to digital converter converts the analog distance signal to a digital distance signal for use by the programmable processing unit.

8. The measurement device according to claim 1, further comprising a mode selection button for selecting a measurement output mode.

9. The measurement device according to claim 8, wherein the measurement output mode is selected from a set of modes, the set of modes including English measurements, metric measurements and comparative measurements.

10. The measurement device according to claim 1, further comprising a calibrate control for calibrating the measurement device to a known distance as measured between the measurement points whereby the scale is automatically set based upon the known distance.

11. The measurement device according to claim 1, further comprising an output port for transmitting a distance measurement signal to a peripheral device.

12. The measurement device according to claim 1, further comprising an input port for programming the measurement device.

13. The measurement device according to claim 1, further comprising a handle, the handle adapted to prevent movement of the legs.

14. A measurement device comprising,
a pair of legs, each leg having a measurement point and a fulcrum end, the fulcrum ends each providing a pivot point for the respective legs so that the measurement points are adapted to arcuately move apart from one another;
a transducer assembly connected to at least one of the legs and adapted to measure leg displacement and generate a distance signal, the transducer assembly being an optical sensor adapted to sense motion of a wheel, the wheel being actuated by at least one of the legs, and the distance signal being an analog distance signal;
an analog to digital converter for converting the analog distance signal to a digital distance signal;
a programmable processing unit adapted to process the digital distance signal and display a distance measurement on an electronic display;
a mode selection control for selecting a measurement output mode;
a scale control, the scale control for selecting a scale value so that the programmable processing unit compensates for a scale associated with a measurement taken between the measurement points and displays an unscaled measurement on the display, wherein the scale lacks predetermined scale values, such that the scale value is set, based on said measurement, to any value within a given range;
an output port for transmitting a distance measurement signal to a peripheral device;
a handle, the handle adapted to prevent movement of the legs; and
a housing, the housing for retaining the fulcrum ends and the handle; and the display, the mode selection control, the calibrate control, the scale control, and the output port being mounted on the housing.

15. The measurement device according to claim 14, wherein the wheel has a series of scores, the scores being counted by the optical sensor as the wheel is actuated.

16. The measurement device according to claim 14, wherein the programmable processing unit is programmed to compensate for an arcuate path of the measurement points.

17. The measurement device according to claim 14, wherein the legs move independently of each other.

18. The measurement device according to claim 14, further comprising a gearing assembly connected to each of the legs so that movement of the legs depend on each other.

19. The measurement device according to claim 14, wherein the measurement output mode is selected from a set of modes, the set of modes including English measurements, metric measurements and comparative measurements.

20. A measurement device comprising,
a pair of legs, each leg having a measurement point and a fulcrum end, the fulcrum ends each providing a pivot point for a respective one of said legs so that the measurement points are adapted to arcuately move apart from one another;
a transducer assembly connected to at least one of the legs and adapted to measure leg displacement and generate a distance signal;
a programmable processing unit adapted to process the distance signal and display a distance measurement on an electronic display, wherein a scale value lacks predetermined values so that the scale value can be any value within a given range, such that the programmable processing unit compensates for a scale associated with a measurement taken between the measurement points and displays an unscaled measurement on the display; and
a control for calibrating the measurement device to a known distance as measured between the measurement points whereby the scale is automatically adjusted.

* * * * *